(12) United States Patent
Cummings

(10) Patent No.: US 11,164,443 B2
(45) Date of Patent: Nov. 2, 2021

(54) ACTIVE CARE CONTROL METHOD, ELECTRONIC CONTROL DEVICE, CENTRAL GATEWAY DEVICE AND SERVER

(71) Applicant: Caroma Industries Limited, Bella Vista (AU)

(72) Inventor: Stephen John Cummings, East Mona Vale (AU)

(73) Assignee: Caroma Industries Limited, Queensland (AU)

( * ) Notice: Subject to any disclaimer, the term of this patent is extended or adjusted under 35 U.S.C. 154(b) by 0 days.

(21) Appl. No.: 16/639,301

(22) PCT Filed: Aug. 15, 2018

(86) PCT No.: PCT/AU2018/000138
§ 371 (c)(1),
(2) Date: Feb. 14, 2020

(87) PCT Pub. No.: WO2019/033145
PCT Pub. Date: Feb. 21, 2019

(65) Prior Publication Data
US 2020/0265704 A1    Aug. 20, 2020

(30) Foreign Application Priority Data

Aug. 16, 2017  (AU) .................................. 2017903296

(51) Int. Cl.
*H04M 1/72418* (2021.01)
*H04W 4/90* (2018.01)
*H04W 4/02* (2018.01)
*G16H 50/20* (2018.01)
*G16H 40/67* (2018.01)
(Continued)

(52) U.S. Cl.
CPC ...... *G08B 25/016* (2013.01); *H04M 1/72418* (2021.01); *H04W 4/02* (2013.01); *H04W 4/90* (2018.02)

(58) Field of Classification Search
CPC .............................. A47J 31/56; G08B 25/016
See application file for complete search history.

(56) References Cited

U.S. PATENT DOCUMENTS 7,113,090 B1 *  9/2006  Saylor .............. G08B 13/19682
340/5.33
2007/0273504 A1   11/2007  Tran
(Continued)

OTHER PUBLICATIONS

International Search Report and Written Opinion, dated Oct. 16, 2018 for International Application PCT/AU2018/000138, 10 pages.
(Continued)

*Primary Examiner* — Joseph H Feild
*Assistant Examiner* — Pameshanand Mahase
(74) *Attorney, Agent, or Firm* — Seed IP Law Group LLP

(57) ABSTRACT

A method for detecting an assistance indicator in a physical consumable usage environment, wherein the method comprises the steps of: detecting an assistance indicator using an electronic control device associated with at least one physical consumable provisioning device; generating an alert based on detection of the assistance indicator; and communicating the alert to a registered device that is associated with the physical consumable provisioning device.

15 Claims, 3 Drawing Sheets

(51) Int. Cl.
    *G06Q 50/06*    (2012.01)
    *G08B 21/22*    (2006.01)
    *G08B 25/01*    (2006.01)

(56) References Cited

U.S. PATENT DOCUMENTS

| | | | |
|---|---|---|---|
| 2008/0001735 A1 | 1/2008 | Tran | |
| 2012/0234409 A1* | 9/2012 | Klicpera | G01F 15/0755 137/551 |
| 2013/0213892 A1* | 8/2013 | Henthorne | B01D 61/025 210/650 |
| 2014/0352412 A1* | 12/2014 | Riviere | G01N 35/1095 73/64.56 |
| 2017/0085083 A1* | 3/2017 | Berkcan | G01F 15/00 |
| 2017/0085966 A1* | 3/2017 | Berkcan | G01F 15/075 |
| 2017/0161004 A1* | 6/2017 | Lee | H04W 4/70 |

OTHER PUBLICATIONS

International Preliminary Report on Patentability, completion date Dec. 6, 2019 for International Application PCT/AU2018/000138, 5 pages.
New Zealand Search Report, dated Dec. 8, 2020, for New Zealand Application No. 761201, 3 pages.
Singapore Search Report, dated Mar. 29, 2021, for Singapore Application No. 11202001171R. 4 pages.

\* cited by examiner

ACTIVE CARE CONTROL METHOD, ELECTRONIC CONTROL DEVICE, CENTRAL GATEWAY DEVICE AND SERVER

TECHNICAL FIELD

The present invention relates generally to an active care control method, electronic control device, central gateway device and server.

BACKGROUND

In certain facilities where people live who require supervision or monitoring for health or care reasons, when such a person becomes incapacitated and requires assistance, it is not always easy for that person to indicate to a relevant authority or authorised carer that assistance is required. For example, in healthcare facilities and aged care facilities etc., providing specialised equipment, such as alarm buttons, usually requires the incapacitated person to move to the alarm button to activate the alarm.

In an aged car facility for example, residents may live semi-autonomously in their own unit. Many accidents occur in wet environments such as the bathroom. However, when an accident occurs, the alarm button may be located at a point that is inaccessible to the incapacitated resident. Similar scenarios are also envisioned in other environments where other physical consumables are provided, such as gas and electricity.

SUMMARY

It is an object of the present invention to substantially overcome, or at least ameliorate, one or more disadvantages of existing arrangements.

Disclosed are arrangements which seek to address the above problems by providing an alert/alarm system and method that can be easily activated by a user. The alert/alarm system and method may utilise modified physical consumable monitoring technology to forward a generated alert/alarm to a registered device via existing infrastructure.

According to a first aspect of the present disclosure, there is provided a method for detecting an assistance indicator in a physical consumable usage environment, wherein the method comprises the steps of: detecting an assistance indicator using an electronic control device associated with at least one physical consumable provisioning device; generating an alert based on detection of the assistance indicator; and communicating the alert to a registered device that is associated with the physical consumable provisioning device.

The method may include the step of generating the assistance indicator using a portable electronic communication device.

The method may include the steps of wirelessly transmitting the assistance indicator to a gateway device in a building management system, and generating the alert at the gateway device.

The method may include the steps of wirelessly transmitting the assistance indicator to a server in a building management system, and generating the alert at the server.

The method may include the step of associating a unique ID of the electronic control device with the assistance indicator to identify one or more of a user, or location, of the electronic control device.

The method may include the step of associating a unique ID of the physical consumable provisioning device with the assistance indicator to identify one or more of a user, or location, of the physical consumable provisioning device.

According to a second aspect of the present disclosure, there is provided an electronic control device comprising a processor and a memory, wherein the memory comprises software code arranged to cause the processor to detect an assistance indicator associated with at least one physical consumable provisioning device; generate an alert based on detection of the assistance indicator; and communicate the alert to a registered device that is associated with the physical consumable provisioning device.

The electronic control device may be part of or integrated with one or more of an electrical, gas or water provisioning device.

The electronic control device may be arranged to communicate the alert to the registered device via a central gateway device and a server.

According to a third aspect of the present disclosure, there is provided a central gateway device in a building management system, wherein the central gateway device comprises a processor and memory, wherein the memory comprises software code arranged to cause the processor to detect an assistance indicator associated with at least one physical consumable provisioning device; generate an alert based on detection of the assistance indicator; and communicate the alert to a registered device that is associated with the physical consumable provisioning device.

The central gateway device may be arranged to communicate the alert to the registered device via a server.

According to a fourth aspect of the present disclosure, there is provided a server in communication with a building management system, wherein the server comprises a processor and memory, wherein the memory comprises software code arranged to cause the processor to detect an assistance indicator associated with at least one physical consumable provisioning device; generate an alert based on detection of the assistance indicator; and communicate the alert to a registered device that is associated with the physical consumable provisioning device.

Other aspects are also disclosed.

BRIEF DESCRIPTION OF THE DRAWINGS

At least one embodiment of the present invention will now be described with reference to the drawings and appendices, in which.

DETAILED DESCRIPTION INCLUDING BEST MODE

The herein description provides details of a method, system, and associated components that provide active care to one or more individuals. The term "active" is intended to mean that care is provided upon activation by the user. That is, the user actively indicates that care is specifically required.

Figure 1:
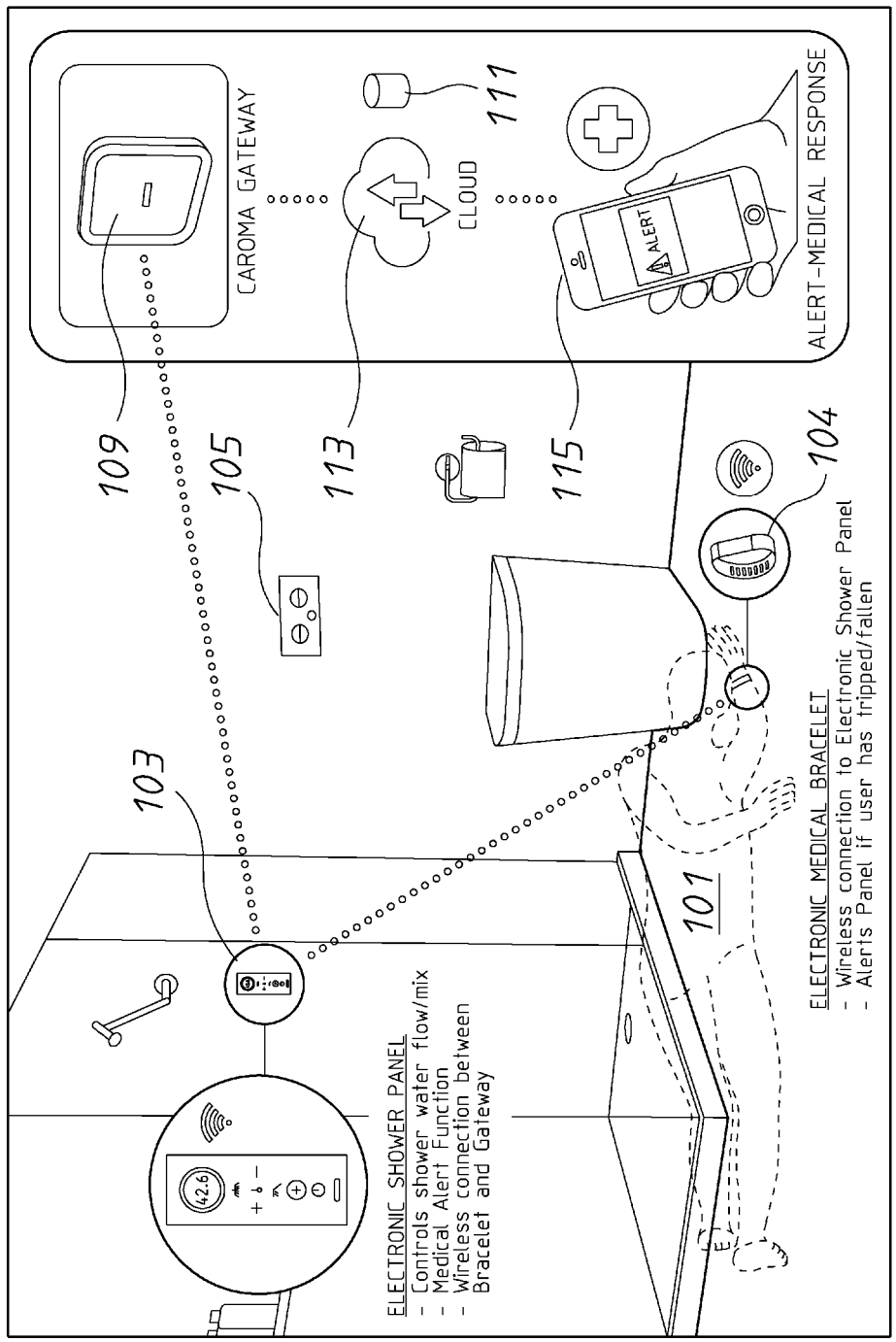
FIG. 1 shows components forming at least part of a building management system for monitoring an alert/alarm according to the present disclosure.

FIG. 1 shows an example arrangement of various electronic control devices for use by a user 101 to control water provisioning devices, such as an electronic shower unit 103 and an electronic toilet flush 105, which are used in a physical consumable usage environment, such as a bathroom 107. Another example of an electronic control device includes an electronic tap ware device.

Each of these electronic control devices includes an electronic system that is arranged to control usage of the water that the device is using. Further, the electronic control device may also detect and/or monitor usage of the water that the device is using in order to generate usage data associated with that device. At least one of the electronic control devices has a wireless receiver that can receive wireless RF signals, such as Bluetooth protocol signals. One or more of the electronic control devices may be part of a building management system (BMS).

The electronic system in each electronic control device is also arranged to wirelessly communicate with a central gateway device 109. For example, the electronic control device may wirelessly communicate using Bluetooth or a Wi-Fi connection. Each electronic control device may have a unique ID in order for the central gateway device to associate the received data with that electronic control device.

The central gateway device is arranged to communicate with a server 111 via the Internet 113. The central gateway device may be part of a building management system (BMS). The central gateway device may connect with multiple electronic control devices throughout a single building, for example, in multiple bathrooms in a single aged care facility. There may also be multiple central gateway devices that are used where each connects to a group of electronic control devices located in one or more groups of bathrooms.

The central gateway device is connected to the Internet (e.g. via a local wireless modem built into the device, a local independent wirelessly connected modem, a 3G/4G data enabled connection (e.g. via a dongle or the like, via a wired connection to a modem, or via an ad-hoc connection (e.g. Bluetooth) to a smart telephone).

The server 111 is arranged to communicate with one or more registered devices 115, which may be, for example, in the form of a smart phone, a laptop, tablet, PC or any other consumable electronic device that can communicate with the server.

The devices may be registered by providing details associated with the device to a server via a website. The details may include the number of the device (if a telephone), IP address or location, ID number etc. Further, when registering the device, details of the user of the consumable provisioning device may be provided, such as the user's location, address, name, contact number etc. Further, when registering the device, details of the consumable provisioning device may also be provided, such as the device's unique ID number, location, type etc. This information is stored by the server to enable any alerts or alarms associated with a user or consumable provisioning device to be communicated to the correct registered device.

The user 101, such as a resident in an aged car facility, has upon themselves a portable electronic communication device 104 that is enabled to wirelessly communicate an assistance indicator that the user 101 requires assistance upon activation by the user (e.g. by generating an assistance indicator mode). This communication device 104 may be a wearable device. The assistance indicator is wirelessly communicated to one or more of the electronic control devices (103, 105). In this example, the assistance indicator is wirelessly communicated to the electronic shower panel 103 by the wearable device 104 using a Bluetooth protocol. When using Bluetooth, the wearable device 104 and the wireless receiver of the electronic shower panel 103 would be paired prior to use. It will be understood that alternative wireless communications may also be used such as Wi-Fi etc.

The assistance indicator may be in any suitable format that enables a communication to be sent from the portable electronic communication device to the electronic control device.

In one example, the initial communication of the assistance indicator from the portable electronic communication device may merely indicate that assistance is required without identifying the user or the portable electronic communication device (other than the minimum identification requirement to enable the communication to occur between the portable electronic communication device and the electronic control device). In this example, the communication is received by the electronic control device and a unique ID associated with the electronic control device is subsequently attached (or appended) to, or otherwise associated with, the assistance indicator to identify where assistance is required. For example, the unique ID, forming part of the assistance indicator, may be used by the central gateway device, the server or the registered device to determine the location of the electronic control device in order to identify the location of the associated user of the electronic control device.

As a further example, a unique ID associated with the physical consumable provisioning device may be attached (or appended) to, or otherwise associated with, the assistance indicator by the electronic control device to identify where assistance is required. For example, the unique ID, forming part of the assistance indicator, may be used by the central gateway device, the server or the registered device to determine the location of the physical consumable provisioning device in order to identify the location of the associated user of the physical consumable provisioning device.

It will be understood that one or more of the electronic control devices may be used to communicate with one or more portable electronic communication devices 104.

Each portable electronic communication device 104 may have a unique ID that is registered when paired with the associated electronic control device. The portable electronic communication device 104 is arranged to communicate an assistance indicator to the associated electronic control device upon activation by a user of the portable electronic communication device 104. Further details are provided herein.

Figure 2:
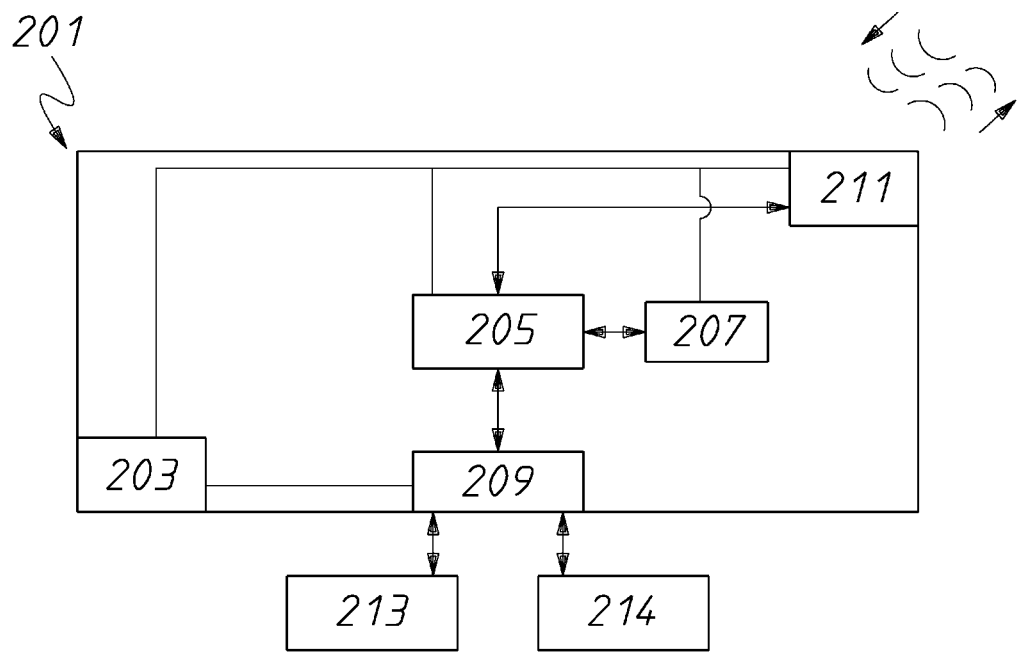
FIG. 2 shows a physical consumable monitoring device according to the present disclosure.

Details of an example electronic control device incorporated within or in communication with the consumable electronic device are provided in FIG. 2.

FIG. 2 shows a block diagram of an example electronic control device 201 which may, for example, be one of the electronic control devices (e.g. 103, 105) for controlling operation of one or more bathroom products (provisioning devices), or be part of such an electronic control device (103, 105).

The control device 201 has a power unit 203 that provides power to a processor 205, a memory 207, an input/output (I/O) port 209 and a transceiver module 211.

The memory 207 stores an algorithm in the form of a software program to cause the processor 205 to operate according to defined instructions. The memory 207 may also be used to store (temporarily or semi-permanently) data associated with the operations of the processor 205. This data may include one or more assistance indicators, unique IDs, provisioning device control data (used to generate control signals), and usage data.

The control device 201 may be connected to one or more taps, shower units and toilet flush units as well as any other type of bathroom product that uses water. The control device 201 may be used by a user to control the use of the bathroom product using control signals, such as switching the flow of water in the bathroom product on and off etc. The control device 201 may be arranged to monitor the provision of the physical consumable. That is, usage data for the provision of the physical consumable may be monitored and recorded.

The I/O port 209 outputs one or more control signals to control how the physical consumable is provided by the provisioning device 214. For example, where the physical consumable is water, the control signals may determine whether water is provided, how much water is provided, the amount of water flow etc. The I/O port 209 may connect to a sensor 213 that senses usage of the physical consumable, such as water. Any known sensor or sensing system may be used to detect the provision of the physical consumable. The I/O port may receive sensor data from the sensor, where the sensor data is based on the usage of the consumable.

The transceiver module 211 connects and communicates data with the central gateway device 109. This data may include one or more of assistance indicator(s), unique IDs, alert data, alarm data, usage data, or any other data that has been generated or obtained by the electronic control device.

Figure 3:
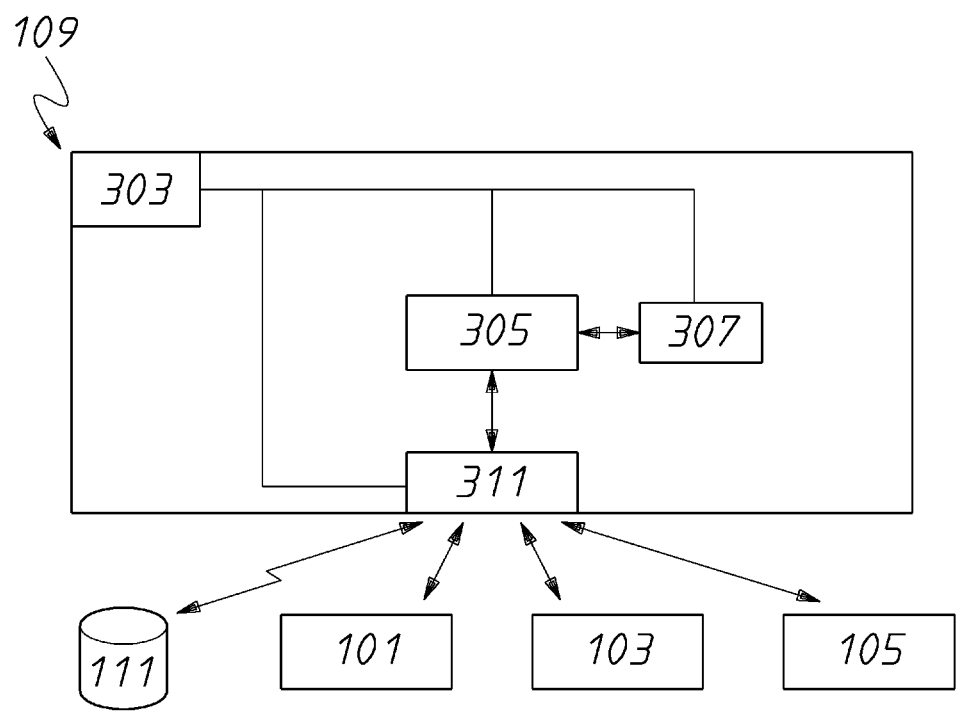
FIG. 3 shows a gateway device forming at least part of a building management system according to the present disclosure.
Figure 4:
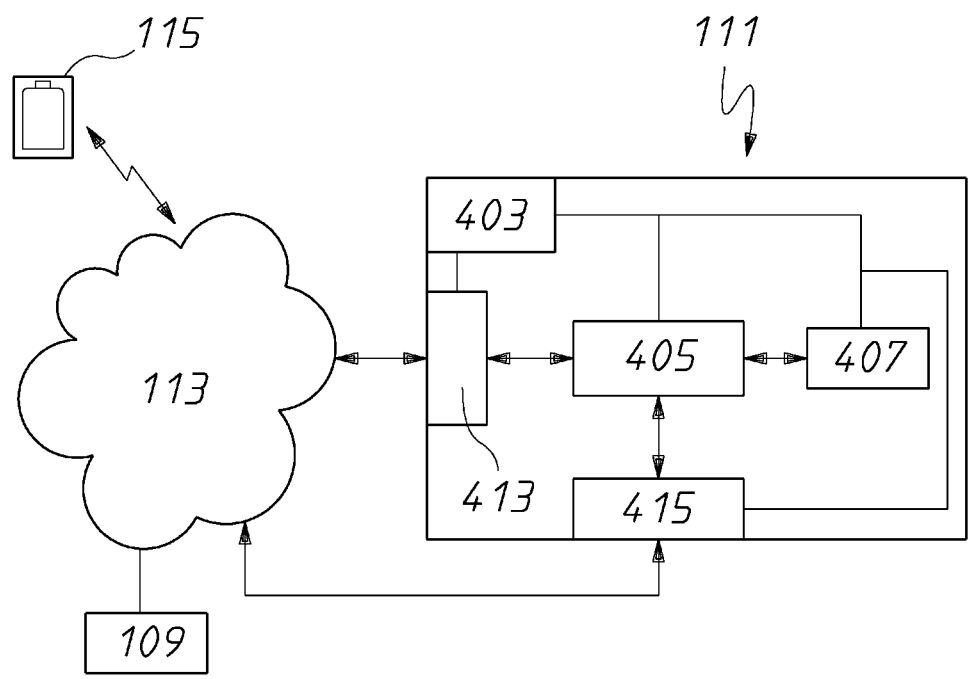
FIG. 4 shows a server forming at least part of a building management system according to the present disclosure.

An example central gateway device and an example server are provided in FIGS. 3 and 4 respectively.

FIG. 3 shows a block diagram of a central gateway device 109. The central gateway device may be part of a building management system (BMS).

The central gateway device 109 has a power unit 303 that provides power to a processor 305, memory 307 and a transceiver module 311.

The memory 307 stores an algorithm in the form of a software program to cause the processor 305 to operate according to defined instructions. The memory 307 may also be used to store (temporarily or semi-permanently) data associated with the operations of the processor 305. This data may include one or more of assistance indicator(s), unique IDs, alert data, alarm data, usage data etc.

The transceiver module 311 connects and communicates data with one or more electronic control devices (103, 105, 201). This data may include one or more of assistance indicator(s), unique IDs, usage data, alert data, alarm data, or any other data that has been generated or obtained by the central gateway device 109.

The transceiver module 311 also connects and communicates data with one or more servers 111. This data may also include one or more of assistance indicator(s), unique IDs, usage data, alert data, alarm data, or any other data that has been generated or obtained by the central gateway device 109. The communication with the server may be via a modem or any other suitable communication means to enable the central gateway device to communicate with the server. For example, the central gateway device may communicate with the server via the Internet using any suitable communication protocols or messages.

FIG. 4 shows a block diagram of a server 111. The server may be part of a building management system (BMS).

The server 111 has a power unit 403 that provides power to a processor 405, memory 407, an input module 413 and an output module 415.

The memory 407 stores an algorithm in the form of a software program to cause the processor 405 to operate according to defined instructions. The memory 407 may also be used to store (temporarily or semi-permanently) data associated with the operations of the processor 405. This data may include assistance indicator(s), unique IDs, or usage data associated with one or more bathroom products. The memory 407 may be used in conjunction with other storage modules (not shown) and databases.

The input module 413 of the server 111 connects and receives data from one or more central gateway devices 109 either directly or via a building management system. This data may include one or more of assistance indicator(s), unique IDs, usage data, alert data, alarm data, or any other data that has been generated or obtained by the central gateway device 109, or an electronic control device (103, 105, 201). The communication between the server and the central gateway device may utilise any suitable form of communication protocols to enable the server to communicate with the central gateway device. For example, the server may communicate with the central gateway device via the Internet using any suitable communication protocols or messages.

The output module 415 of the server 111 connects and communicates data to one or more registered devices 115. This data may include one or more of assistance indicator(s), unique IDs, usage data, alert data, alarm data, or any other data that has been generated or obtained by the server 111. The communication with the server may be via an output port or any other suitable communication device to enable the server to communicate with the registered devices. For example, the server may communicate with the registered devices via the Internet using any suitable communication protocols or messages.

Figure 5:
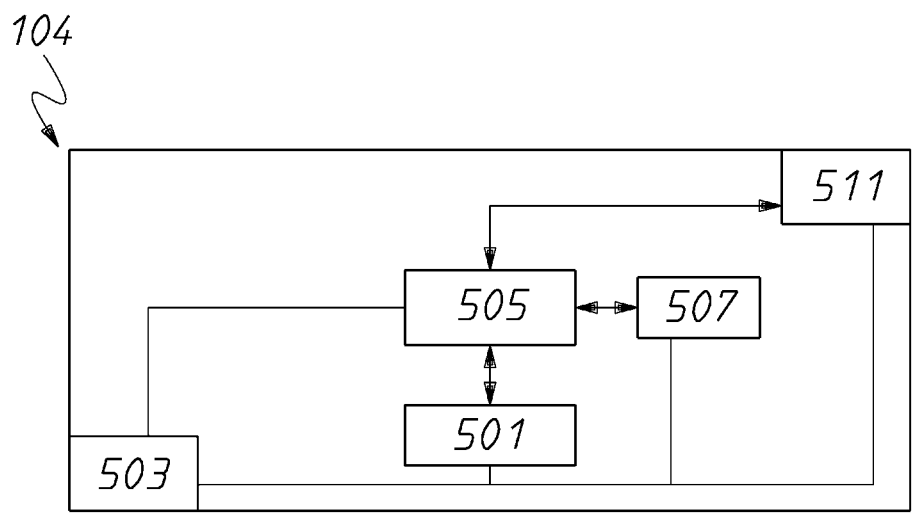
FIG. 5 shows a portable electronic communication device according to the present disclosure.

FIG. 5 shows an example portable electronic communication device 104. The portable electronic communication device 104 has a power unit 503 that provides power to a processor 505, a memory 507, an assistance indicator generator 501 and a wireless transceiver 511. The portable electronic communication device may be, for example, a wearable device. The wearable device may be a medical bracelet, a tracking device, a health monitoring device or the like. The wearable device may be incorporated as part of another device such as a smart watch etc. Multiple portable electronic communication devices may be used in one environment. Each device has a unique ID associated with it. Therefore, there may be multiple users of the herein described system within a single dwelling or facility.

The assistance indicator generator 501 is a module that enables a user or wearer of the portable electronic communication device to generate an assistance indicator. An assistance indicator may be generated by the generator 501 by, for example, pressing a dedicated button or sequence of buttons. Alternatively, the assistance indicator may be generated by the generator 501 by selection of a dedicated menu option. As a further option, a pressure sensor may be used to activate the assistance indicator generator 501 to generate the assistance indicator based on detection of a defined pressure sequence or defined pressure activation period. For example, applying pressure for a defined period of time (e.g. 5 seconds) to a pressure sensor that is part of the assistance indicator generator 501 may generate the assistance indicator.

The assistance indicator may be stored in the memory of the portable electronic communication device for transmission to one or more of the electronic control devices at a later time.

The assistance indicator may be automatically wirelessly transmitted to one or more of the electronic control devices upon generation.

The various components described above in relation to FIGS. 1-5 are used to monitor for an assistance indicator that is generated by the portable electronic communication device 104.

If it is determined that an assistance indicator has been generated, then an alert and/or alarm may be generated and sent to one or more registered devices that are associated with the user or usage of the consumable. The alert or alarm may be, for example, one or more of an email, an SMS, a telephone calls, an electronic alert, a communication to a software program operating on an electronic device etc. Any of the electronic control device, central gateway device and server may i) determine whether an assistance indicator has been generated, ii) communicate that the assistance indicator has been generated, iii) generate an alert or alarm and iv) communicate an alert or alarm.

Several examples are now provided to show how the herein described system, or variations of it, may operate in order to detect the assistance indicator and generate an associated alert or alarm.

The following example describes how an electronic control device may detect the assistance indicator in a bathroom environment.

The electronic control device may be associated with, part of, or integrated with one or more physical consumable provisioning devices.

The electronic control devices may be a device such as a shower unit 103 or flush unit 105 as shown in FIG. 1 (or a tap ware unit, for example).

The electronic control device 201 may detect that an assistance indicator has been generated in a number of different ways.

For example, the portable electronic communication device 104 may automatically communicate the assistance indicator to the electronic control device 201 after the assistance indicator has been generated by the portable electronic communication device 104.

As another example, the electronic control device 201 may poll the portable electronic communication device at regular intervals to see if an assistance indicator has been generated. That is, the polling communication enquires with the processor 505 of the portable electronic communication device 104 to see if an assistance indicator has been generated, and if so, the assistance indicator is retrieved from memory 507 and wirelessly communicated to the electronic control device 201.

The electronic control device 201 may then generate an alert or alarm based on the received assistance indicator.

The generated alert may be in any suitable format. The alert is then communicated by the electronic control device to the central gateway device. The central gateway device then communicates the alert to the server. The server then communicates the alert to a registered device that has been registered with that particular electronic control device or associated consumable provisioning device. For example, the registered device may be a mobile telephone that has been registered by an aged car facility or a health facility.

The following example describes how a central gateway device may generate an alarm based on an assistance indicator.

The assistance indicator may be communicated to the central gateway device 109. The central gateway device 109 may then generate an alert or alarm based on the received assistance indicator.

As discussed above, the generated alert may be in any suitable format. The alert is then communicated by the central gateway device to the server. The server may then communicate the alert to a registered device that has been registered with that particular electronic control device or associated consumable provisioning device. For example, the registered device may be a mobile telephone that has been registered by an aged car facility or a health facility.

The following example describes how a server may generate an alarm based on an assistance indicator.

The assistance indicator may be communicated to the server 113 by the central gateway device 109. The server 113 may then generate an alert or alarm based on the received assistance indicator.

As discussed above, the generated alert may be in any suitable format. The server may then communicate the alert to a registered device that has been registered with the associated electronic control device or consumable provisioning device. For example, the registered device may be a mobile telephone that has been registered by an aged car facility or a health facility.

It will be understood that one or more of the electronic control device, central gateway device and server may perform part of or the entire process used to generate an alarm or alert.

In accordance with any one of examples described herein, different levels of alerts/alarms may be generated based on the assistance indicator received from the portable electronic communication device. For example, the assistance indicator may indicate that the user needs help, is in danger, or in critical danger etc.

Specific people or groups of people may be sent the alert or alarm based on the associated unique ID or the list of registered devices associated with the unique ID. For example, registered devices operators of the care facility, an ambulance service, a specific doctor, or relatives may be sent the alert or alarm.

In the examples described above, the bathroom is an example of a physical consumable usage environment. It will be understood that the methods and systems described herein may be applied to other physical consumable usage environments such as, for example, other water usage environments, gas usage environments and electricity usage environments where control devices are used to control the provision of the physical consumable.

INDUSTRIAL APPLICABILITY

The arrangements described are applicable to the computer and data processing industries and particularly for the industries concerned with detecting whether a person is incapacitated or requires assistance.

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. A method of detecting an assistance indicator in a water usage environment in a healthcare facility or aged care facility, wherein the method comprises the steps of:
   detecting the assistance indicator using an electronic control device arranged to control at least one water provisioning device in the water usage environment, wherein the electronic control device comprises an electronic system arranged to control usage of water by the water provisioning device, wherein the assistance indicator is generated by a portable electronic communication device, and the assistance indicator indicates a user of the portable electronic communication device in the water usage environment requires assistance;
   generating an alert based on the electronic control device detecting the assistance indicator; and
   communicating the alert to a registered device that is associated with the water provisioning device.

2. The method of claim 1 further comprising the step of generating the assistance indicator using the portable electronic communication device.

3. The method of claim 1 further comprising the steps of:
   wirelessly transmitting the assistance indicator to a gateway device in a building management system, and
   generating the alert at the gateway device.

4. The method of claim 1 further comprising the steps of:
   wirelessly transmitting the assistance indicator to a server in a building management system, and
   generating the alert at the server.

5. The method of claim 1 further comprising the step of associating a unique ID of the electronic control device with the assistance indicator to identify one or more of a user, or location, of the electronic control device.

6. The method of claim 1 further comprising the step of associating a unique ID of the water provisioning device with the assistance indicator to identify one or more of a user, or location, of the water provisioning device.

7. The method of claim 6, wherein the unique ID of the water provisioning device is appended to the assistance indicator to indicate the location where assistance is required.

8. An electronic control device arranged to control at least one water provisioning device in a water usage environment in a healthcare facility or aged care facility, the electronic control device comprising a processor, a memory and an electronic system arranged to control usage of water by the water provisioning device, wherein the memory comprises software code arranged to cause the processor to:
   detect an assistance indicator generated by a portable electronic communication device, and the assistance indicator indicates a user of the portable electronic communication device in the water usage environment requires assistance;
   generate an alert based on the detection of the assistance indicator by the electronic control device; and
   communicate the alert to a registered device that is associated with the water provisioning device.

9. The electronic control device of claim 8, wherein the electronic control device is part of or integrated with the water provisioning device.

10. The electronic control device of claim 8, wherein the electronic control device is arranged to communicate the alert to the registered device via a central gateway device and a server.

11. The electronic control device of claim 8, wherein the electronic control device is arranged to associate a unique ID of the water provisioning device with the assistance indicator to identify one or more of a user, or location, of the water provisioning device.

12. The electronic control device of claim 11, wherein the electronic control device is arranged to append a unique ID of the water provisioning device to the assistance indicator to indicate the location where assistance is required.

13. A central gateway device in a building management system, wherein the central gateway device comprises a processor and memory, wherein the memory comprises software code arranged to cause the processor to:
   detect an assistance indicator using an electronic control device, wherein the assistance indicator is generated by a portable electronic communication device, and the assistance indicator indicates a user of the portable electronic communication device in a water usage environment requires assistance, wherein the electronic control device is arranged to control at least one water provisioning device in the water usage environment, and wherein the electronic control device comprises an electronic system arranged to control usage of water by the water provisioning device;
   generate an alert based on the detection of the assistance indicator by the electronic control device; and
   communicate the alert to a registered device that is associated with the water provisioning device.

14. The central gateway device of claim 13, wherein the central gateway device is arranged to communicate the alert to the registered device via a server.

15. A server in communication with a building management system, wherein the server comprises a processor and memory, wherein the memory comprises software code arranged to cause the processor to
   detect an assistance indicator using an electronic control device, wherein the assistance indicator is generated by a portable electronic communication device, and the assistance indicator indicates a user of the portable electronic communication device in a water usage environment requires assistance, wherein the electronic control device is arranged to control at least one water provisioning device in the water usage environment, and wherein the electronic control device comprises an electronic system arranged to control usage of water by the water provisioning device;
   generate an alert based on the detection of the assistance indicator by the electronic control device; and
   communicate the alert to a registered device that is associated with the water provisioning device.

* * * * *